United States Patent
Surana et al.

(10) Patent No.: US 7,550,640 B2
(45) Date of Patent: Jun. 23, 2009

(54) HIGH VISCOSITY PAOS BASED ON 1-DECENE/1-DODECENE

(75) Inventors: Phil Surana, Somerset, NJ (US); Norman Yang, Westfield, NJ (US); Pramod J. Nandapurkar, Plainsboro, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 610 days.

(21) Appl. No.: 11/036,904

(22) Filed: Jan. 14, 2005

(65) Prior Publication Data

US 2006/0161034 A1 Jul. 20, 2006

(51) Int. Cl.
    *C07C 2/08* (2006.01)
(52) U.S. Cl. .......... 585/532; 585/520; 585/530
(58) Field of Classification Search .......... 585/520, 585/532, 533
    See application file for complete search history.

(56) References Cited

U.S. PATENT DOCUMENTS

| | | | |
|---|---|---|---|
| 3,149,178 A | 9/1964 | Hamilton et al. | 260/683.9 |
| 3,382,291 A | 5/1968 | Brennan | 260/683.15 |
| 3,742,082 A | 6/1973 | Brennan | 260/683.9 |
| 3,780,128 A | 12/1973 | Shubkin | 260/683.9 |
| 4,172,855 A | 10/1979 | Shubkin et al. | 585/16 |
| 4,533,782 A | 8/1985 | Merijanian | 585/520 |
| 4,956,122 A | 9/1990 | Watts et al. | 252/565 |
| 5,196,635 A * | 3/1993 | Kumar et al. | 585/532 |
| 5,284,988 A * | 2/1994 | Schaerl et al. | 585/525 |
| 6,395,948 B1 | 5/2002 | Hope et al. | 585/510 |
| 6,646,174 B2 | 11/2003 | Clarembeau | 585/525 |
| 6,686,511 B2 | 2/2004 | Miller et al. | 585/519 |
| 6,706,828 B2 | 3/2004 | DiMaio | 526/160 |
| 6,713,582 B2 | 3/2004 | DiMaio et al. | 526/281 |
| 2002/0128532 A1 | 9/2002 | Hope et al. | |
| 2002/0193650 A1 | 12/2002 | Goze et al. | 585/521 |

FOREIGN PATENT DOCUMENTS

| EP | 0 741 120 | 6/1996 |
|---|---|---|
| EP | 1 342 707 | 10/2003 |
| WO | WO 99/38938 | 8/1999 |
| WO | WO 02/088205 | 7/2002 |

OTHER PUBLICATIONS

Russian Abstract 2212936, Savchenko et al., Sep. 27, 2003.
Japanese Abstract 01-095108, Shingen, Apr. 13, 1989.

* cited by examiner

*Primary Examiner*—In Suk Bullock
(74) *Attorney, Agent, or Firm*—Nancy T. Krawczyk; Andrew B. Griffis

(57) ABSTRACT

This invention relates to the use of 1-decene/1-dodecene olefin mixture to produce high viscosity polyalphaolefins (PAOs) having a viscosity of from about 40 cSt to about 100 cSt at 100° C. (ASTM D-445) and a number average molecular weight of between about 1200 to about 4000, particularly useful as lubricant base stocks.

9 Claims, No Drawings

HIGH VISCOSITY PAOS BASED ON 1-DECENE/1-DODECENE

FIELD OF THE INVENTION

This invention relates to the use of 1-decene/1-dodecene olefin mixtures to produce high viscosity polyalphaolefins (PAOs). The products are particularly useful as lubricant base stocks.

BACKGROUND OF THE INVENTION

PAOs comprise a class of hydrocarbon lubricants which has achieved importance in the lubricating oil market. These materials are typically produced by the catalytic oligomerization (polymerization to low-molecular-weight products) of α-olefins typically ranging from 1-octene to 1-dodecene, with 1-decene being a preferred material, although polymers of lower olefins such as ethylene and propylene may also be used, including copolymers of ethylene with higher olefins, as described in U.S. Pat. No. 4,956,122 and the patents referred to therein. PAO products may be obtained with a wide range of viscosities varying from highly mobile fluids of about 2 cSt at 100° C. to higher molecular weight, viscous materials which have viscosities exceeding 100 cSt at 100° C.

The PAO's are typically produced by the polymerization of olefin feed in the presence of a catalyst such as $AlCl_3$ or $BF_3$. Processes for the production of PAO lubricants are disclosed in numerous patents, for example, U.S. Pat. Nos. 3,149,178; 3,382,291; 3,742,082; 3,780,128; 4,172,855 and 4,956,122.

High viscosity PAOs (defined herein as PAOs having a kinematic viscosity at 100° C. of >20 cSt as measured by ASTM D 445) are normally produced via cationic oligomerization of linear alpha olefins. 1-decene is the preferred olefin for oligomerization. PAOs have also been produced using mixtures of olefins containing 1-octene and 1-dodecene.

High viscosity PAOs produced via $AlCl_3$ catalyzed olefin oligomerization have been available commercially for many years, e.g., from ExxonMobil Chemical Company. These PAOs are produced either from 1-decene, or from a mixture of 1-octene/1-dodecene. When oligomerizing olefin mixtures, the composition needs to be carefully controlled to produce PAOs with the desired blend of low temperature properties including pour point, viscosity, and appearance. Typically, use of olefins with molecular weight greater than 1-decene results in PAOs with high pour points. As a result, when oligomerizing olefin mixtures, a combination of low and high molecular weight olefins (with respect to 1-decene) is generally used.

U.S. Pat. No. 4,533,782 is directed to polymerizing cationically polymerizable monomers including C3-C14 linear or branched 1-olefins using a catalyst comprising an aluminum compound of the formula $R_nAlX_{3-n}$ and a compound having the formula R'X (X being a halide in both formulas) in solution.

U.S. Pat. No. 5,196,635 discloses the use of a catalyst prepared by reacting in an organic solvent an aluminum halide and a proton donor useful in oligomerizing C6 to C20 straight chain alpha olefins.

U.S. Pat. No. 6,646,174 teaches a process for oligomerization of 1-dodecene and 1-decene to produce a PAO product having a kinematic viscosity in the range of from about 4 to about 6 cSt at 100° C. and a viscosity index of 130 to 145, and a pour point of –60° C. to –50° C.

U.S. Pat. No. 6,686,511 directed to a process for making a lube base stock having at least four steps, including separation of an olefinic feedstock in a first separator into fractions and contacting a light olefin fraction with a first oligomerization catalyst in a first oligomerization zone to produce a first product, which is subsequently contacted with a medium olefin fraction and an oligomerization catalyst in a second oligomerization zone to produce a second product.

U.S. Pat. No. 6,395,948 discloses the use of an acidic ionic liquid oligomerization catalyst, described by the general formula $Q^+A^-$, for the preparation of high viscosity PAOs from decene or dodecene in the absence of an organic diluent. See also U.S. Application Nos. 2002/0128532 and 2004/0030075.

JP1095108 is directed to a method for manufacturing an olefin oligomer using a Lewis acid and an alkyl cyclohexane.

RU2212936 is directed to a cationic oligomerization of olefins that uses a catalyst containing active aluminum and a co-catalyst that is an organohalide compound RX, where R is a primary, secondary, or tertiary alkyl, allyl, benzyl, acetyl or benzoyl and X is chlorine, bromine or iodine.

Additional patents of interest include WO 99/38938 and U.S. Pat. Nos. 6,706,828 and 6,713,582.

Current practice does not provide enough flexibility in the choice of feed olefin/olefin mixtures that can lead to an economic method of achieving a high viscosity PAO composition having adequate low temperature performance suitable for end use applications such as industrial lubricants.

The present inventors have surprisingly discovered a method of producing high viscosity PAOs having excellent low temperature performance from 1-decene/1-dodecene mixtures.

SUMMARY OF INVENTION

The present inventors have discovered 1-decene/1-dodecene mixtures that can be oligomerized to high viscosity PAOs which may be characterized by a kinematic viscosity of from about 40 to about 100 cSt at 100° C. (ASTM D-445), and in an embodiment possess desired low temperature properties, such as low pour point.

In an embodiment, the process introduces the mixture of olefins with a catalyst into a first reactor to produce a partially reacted product that is fed into a second reactor to complete the reaction. In yet another embodiment, the process uses 3-reactors in series to complete the reaction.

In another embodiment, the process produces a 40 cSt PAO at 100° C. in the absence of a solvent and in still another embodiment, the process produces a 100 cSt PAO at 100° C. using a solvent. In yet another embodiment, the high viscosity PAOs of the present invention have a number average molecular weight of between about 1200 to about 4000.

These and other embodiments, objects, features, and advantages will become apparent as reference is made to the following drawings, detailed description, examples, and appended claims.

DETAILED DESCRIPTION

The invention is directed to mixtures of linear alpha olefins comprising decene and 1-dodecene oligomerized using an aluminum halide complex with water to produce high viscosity PAOs having, in an embodiment, a kinematic viscosity of from about 40 and about 100 cSt at 100° C. (ASTM D-445) and which in an embodiment possess the desired low temperature properties, such as low pour point.

The process according to the invention comprises co-feeding a mixture of linear alpha olefins (LAO) comprising 1-decene and 1-dodecene concurrently with the catalyst. The catalyst may be any known catalyst for the polymerization of LAOs to PAOs, such as $AlCl_3$. Preferably, the catalyst is a complex comprising a proton donor such as water with an aluminum halide, preferably aluminum trichloride-water complex having 0.5 moles of water per mole of aluminum chloride. The reaction may be batch, semi-batch or continuous, in a single or multi-stage reactors. In a preferred embodiment, the mixture of catalyst and linear alpha olefins (LAOs) is preferably fed into a first oligomerization reactor where it is partially reacted and then into a second oligomerization reactor where the reaction may be allowed to continue to completion or where the reaction may be allowed to proceed further and then the mixture of catalyst, linear alpha olefins and oligomers are fed into a third oligomerization reactor where the reaction is completed. Additional oligomerization reactors may be used in series.

The reaction zone may be any reaction means known in the art that provides for the reaction under suitable conditions maintained and controlled so as to provide for the production of oligomers of the LAO feed. The LAO feed comprising a mixture of 1-decene and 1-dodecene and catalyst may be introduced either separately or together into the first reaction zone. It is preferred that the reactors each be equipped with a mixing or stirring means for mixing the feed and catalyst to provide intimate contact. In a more preferred embodiment, continuous stirred tank reactors (CSTRs) are used in series. CSTRs are per se known in the art. Also in a preferred embodiment, no recycle of unconverted monomer is used.

An effective amount of catalyst is provided. One of ordinary skill in the art in possession of the present disclosure can determine an effective amount without undue experimentation. In a preferred embodiment, the catalyst concentration is between 0.5 to 4 wt. % of the total reaction mass (e.g., monomers, catalyst, diluent and/or other optional ingredients). It is known in the art that the addition of aromatics in small amounts improves the oligomerization of LAOs. In the 100 cSt examples below, 0.5 wt. % xylenes was present in the feed.

Reaction conditions are such as to cause effective conversion of monomers to the desired product. Such conditions may also be determined by one of ordinary skill in the art in possession of the present disclosure without undue experimentation. In a preferred embodiment, the reactor temperatures are between about 80 and 140° F. (between about 26 and 60° C.) and residence time of about 1.5 to about 3 hours in reactor one and about 0.5 to about 1.5 hours in reactor 2, if used. The residence time in a third reactor, if used would typically be from about 10 minutes to about 1 hour. The reaction is not particularly pressure-dependent and it is most economical to operate the reactors at a low pressure, preferably from about atmospheric to about 50 psia.

In an embodiment, no solvent is used. In another embodiment, an inert diluent may be used, preferably selected from fluids such as C5-C19 paraffinic hydrocarbons, preferably a C6-C13 paraffinic fluid such as Norpar™ 12 fluid, an aliphatic (paraffinic) solvent having primarily twelve carbon aliphatic compounds, available from ExxonMobil Chemical Company, Baytown, Tex.

The product of the reaction typically comprises C20-24 dimers, C30-36 trimers, C40-48 tetramers, C50-60 pentamers, and C60+ heavies.

The reaction mixture is then distilled to remove unreacted monomeric and dimeric species. In a preferred embodiment, the resulting product is typically hydrogenated to saturate the oligomers to provide a product having a desired viscosity, for example 40 cSt or 100 cSt at 100° C.

EXPERIMENTAL

The following examples are meant to illustrate the present invention and provide a comparison with other methods and the products produced therefrom. Numerous modifications and variations are possible and it is to be understood that within the scope of the appended claims, the invention may be practiced otherwise than as specifically described herein.

The reactions were carried out in a three-neck 5-liter round bottom jacketed glass flask (reactor) that was fitted with a motor driven stirrer and a baffle. A pump circulated chilled water through the jacket to control reaction temperature. About two thousand grams of the LAO feed were charged into a feed burette. In the case of 100 cSt PAO, Norpar™ 12 Fluid was also added to the olefin mixture (25-30 wt. % of olefins) to improve mixing and heat transfer during oligomerization. No diluent was added in the case of the 40 cSt PAO. A pump was used to feed the LAO into the reactor at a controlled rate. The reactor was dried and purged with dry nitrogen to remove moisture before the start of oligomerization. The reactor was continuously purged with small amount of nitrogen during the reaction as well. The desired amount of $AlCl_3$ catalyst, 0.8 to 4.0 wt. % of feed, was pre-weighed and stored in closed glass vials. The $AlCl_3$ is commercially available from numerous sources. The $AlCl_3$ used below was purchased from Gulbrandsen Chemicals. Other cationic oligomerization catalysts such as $AlBr_3$ will also be efficient according to the present investigation. In the case of $AlCl_3$, the present inventors have found that less catalyst is necessary using finer granularity catalyst.

At the start of oligomerization, feed olefin mixture was pumped into the flask for 15 minutes under vigorous agitation, and with cooling water flowing through the jacket. The $AlCl_3$ catalyst from a glass vial was emptied into the reactor next, and a measured amount of DI (deionized) water was injected into the flask via a long needle syringe. The amount of DI water injected corresponded to 0.5 moles of water/mole of $AlCl_3$. The feed was added continuously over a period of two to five hours into the reactor. The required amounts of catalyst and DI water were added at the intervals of 15 minutes. The oligomerization reaction was allowed to proceed additional one to three hours after the olefin and catalyst additions were completed. The reaction temperature ranged between 30° C. to 60° C.

The reaction was quenched by adding the reactor contents into an equal volume of caustic (5 wt. % aqueous sodium hydroxide) solution at 65-70° C. The quenched mass was subsequently washed two times with hot water at 65-70° C. The viscous oil was next separated from the aqueous layer and distilled to remove water, unconverted monomer and dimer (and solvent if present). A material balance on the distillation indicated a feed olefin conversion of 98-99%. The viscous oil was de-chlorinated thermally and hydrogenated over Pd catalyst.

For each of the reported examples below, 100° C. and 40° C. Kinematic Viscosity was measured according to ASTM D-445 at the respective temperatures; Pour Point was determined according to ASTM D-97; and Viscosity Index (VI) was determined according to ASTM D-2270. Number average molecular weight (Mn) was measured by Gel Permeation Chromatography using a Waters 150 gel permeation chromatograph equipped with a differential refractive index (DRI) detector. The numerical analyses were performed using the commercially available standard Gel Permeation chromatography software package.

The following examples are directed to the making of a 40 cSt PAO and comparisons.

Examples 1 & 2

The physical property data for commercial PAOs produced with conventional olefin feed (1-decene for Example 1 and 1-octene/1-dodecene for Example 2) is shown as Examples 1 and 2 in Table 1, below. A pour point of −42° C. is obtained for the product. The Viscosity Index, VI, of the product ranges between 150 to 151.

Example 3

The oligomerization of a 55/45 wt. % mixture of $C_{10}/C_2$ olefins (1-decene and 1-dodecene) was carried out using 1.45 wt. % $AlCl_3$ concentration by the procedure described above. The olefin addition time was 2 hours (add time) while the reaction mass was held (hold time) for an additional hour. The temperature varied between 45° C. to 61° C. during course of reaction. This resulted in a PAO product with a pour point of −42° C. and a VI of 152.

Example 4

The procedure was the same as in Example 3 except that the feed composition was 50/50 wt. % mixture of the $C_{10}/C_{12}$ olefins, the catalyst concentration was 1.33 wt. % $AlCl_3$. The reaction temperature varied between 45° C. to 58° C. The pour point of the product was −42° C. and the VI was 151.

Example 5

The procedure was the same as Example 3 except that the feed composition was 100% $C_{12}$ olefin. The add time was 3 hours, the hold time was 1 hour and the catalyst concentration was 1.3 wt. % $AlCl_3$. The reaction temperature ranged between 45 to 50° C. The pour point of the product was −33° C. VI was 158.

Example 6

The procedure was the same as Example 3 except that the feed composition was 50/50 wt. % mixture of the $C_{12}/C_{14}$ olefins. The add time was 3 hours, the hold time was 1 hour, the catalyst concentration was 1.4 wt. % and the reaction temperature varied between 45 to 50° C. The pour point of the product was −21° C. and the VI was 161.

The results of the above examples are shown in Table 1, below. It is apparent that a carefully controlled composition of $C_{10}/C_{12}$ olefins is needed to produce a 40 cSt PAO with desired low pour point.

TABLE 1

| Example | Feed Olefin | 100° C. Viscosity, cSt | 40° C. Viscosity, cSt | VI | Pour Point, ° C. |
|---|---|---|---|---|---|
| 1 | $C_{10}$ | 39 | 383 | 151 | −42 |
| 2 | 50/50 $C_8/C_{12}$ | 39.5 | 393 | 150 | −42 |
| 3 | 55/45 $C_{10}/C_{12}$ | 39.7 | 386 | 152 | −42 |
| 4 | 50/50 $C_{10}/C_{12}$ | 38.8 | 378 | 151 | −42 |
| 5 | $C_{12}$ | 38.2 | 351 | 158 | −33 |
| 6 | 50/50 $C_{12}/C_{14}$ | 40.5 | 371 | 161 | −21 |

The following examples are directed to the making of 100 cSt PAO and comparisons.

Examples 7 & 8

The physical property data for commercial PAOs produced with conventional olefin feed (1-decene for Example 7 and 1-octene/1-dodecene for Example 8) is shown as Examples 7 and 8 in Table 2 below. A pour point of −33° C. is obtained for the product. The Viscosity Index, VI, of the product is 168.

Example 9

The oligomerization of a 55/45 wt. % mixture of the $C_{10}/C_{12}$ olefins in laboratory was carried out using 2.45 wt. % $AlCl_3$ concentration by the procedure described in the experimental section. The feed add time was three hours while the hold time was two hours. The reaction temperature varied between 37° C. to 45° C. The product PAO had a pour point of −33° C. while the VI was 173.

Example 10

Same as Example 9 except that the feed was a 50/50 wt. % mixture of the $C_{10}/C_{12}$ olefins, the catalyst concentration was 3.0 wt. % $AlCl_3$ and the reaction temperature ranged between 37° C. to 45° C. The product had a pour point of −33° C. while the VI was 173.

Example 11

Same as example 9 except that the feed was 100 wt. % $C_{12}$ olefin. The add time was three hours, the catalyst concentration was 3 wt. % $AlCl_3$ and the reaction temperature was 40 to 45° C. The product had a pour point of −27° C. and a VI of 176.

Example 12

The pour point increased to −21° C. when a 60/40 (wt. %) mixture of $C_{12}/C_{14}$ olefins was used. The oligomerization procedure was the same as in Example 9. The add time was 3 hours, the hold time was 2 hours, and the catalyst concentration was 2.8 wt. %. The product had a VI of 180.

The results of the above examples are shown in Table 2, below. It is apparent that a carefully controlled composition of $C_{10}/C_{12}$ olefins is needed to produce a 100 cSt PAO with desired low pour point. It is also observed that a 100 cSt PAO with desirable low pour point can not be produced by this technology with olefins or olefin mixtures having carbon number greater than 12.

TABLE 2

| Example | Feed Olefin | 100° C. Viscosity cSt | 40° C. Viscosity cSt | VI | Pour Point, ° C. |
|---|---|---|---|---|---|
| 7 | $C_{10}$ | 102 | 1289 | 168 | −33 |
| 8 | 50/50 $C_8/C_{12}$ | 100.5 | 1267 | 168 | −33 |
| 9 | 55/45 $C_{10}/C_{12}$ | 107.2 | 1332 | 173 | −33 |
| 10 | 50/50 $C_{10}/C_{12}$ | 104.8 | 1285 | 173 | −33 |
| 11 | $C_{12}$ | 104 | 1234 | 176 | −27 |
| 12 | 60/40 $C_{12}/C_{14}$ | 106.8 | 1234 | 180 | −21 |

Example 13

The oligomerization of a 55/45 wt. % mixture of the $C_{10}/C_{12}$ olefins in a 2-CSTR commercial set-up was carried out to produce a 40 cSt PAO. The process used an $AlCl_3$ concentration of 1.2 wt. %, a reaction temperature of 50° C., 0.5 mols of water per mole of $AlCl_3$, and a residence time of 2 hr and 1 hr in reactors 1 and 2 respectively. The product PAO had a 100° C. viscosity of 40.19 cST, a VI of 152 and a pour point of −51° C.

Example 14

The same 2-CSTR set-up was also used to produce a 100 cSt PAO using a 55/45 wt. % mixture of the $C_{10}/C_{12}$ olefins. The concentration of $AlCl_3$ was 3.0 wt. %, 0.5 mols of water were used per mole of $AlCl_3$, the reaction temperature was 40° C., the concentration of the diluent (Norpar™12) was 22 wt. % and the residence time in reactors 1 and 2 were 2.5 hr and 1.2 hr respectively. The product PAO had a 100° C. viscosity of 104.2 cSt, a VI of 172 and a pour point of −39° C.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples. Rather, many variations will suggest themselves to those skilled in this art in light of the above detailed description. All such obvious variations are within the full intended scope of the appended claims. Preferred embodiments of the present invention include: a process for producing a polyalphaolefin (PAO) comprising contacting a feed comprising 1-decene and 1-dodecene with an oligomerization catalyst in an oligomerization reaction zone under oligomerization conditions for a time sufficient to produce a PAO having a viscosity of from about 40 cSt to about 100 cSt at 100° C. (ASTM D-445), and a number average molecular weight of between about 1200 to about 4000; more preferred embodiments of this process including at least one of the limitations selected from the following, which may be combined in a manner that would be apparent and practicable to one of ordinary skill in the art in possession of the present disclosure: wherein said feed comprises 10-90% 1-decene monomer units and 90-10% 1-dodecene monomer units, on a molar basis; wherein said feed comprises 25-74% 1-decene monomer units and 75-25% 1-dodecene monomer units, on a molar basis; wherein said feed comprises 40-60% 1-decene monomer units and 60-40% 1-dodecene monomer units, on a molar basis; wherein said feed comprises 45-55% 1-decene monomer units and 55-45% 1-dodecene monomer units, on a molar basis; wherein said PAO has a kinematic viscosity of about 40 cSt at 100° C. (ASTM D-445), a viscosity index of at least about 150 (ASTM D-2270), and a pour point of less than or equal to about −42° C. (ASTM D-97); wherein said PAO has a kinematic viscosity of about 100 cSt at 100° C. (ASTM D-445), a viscosity index of at least about 170 (ASTM D-2270), and a pour point of less than or equal to about −30° C. (ASTM D-97); wherein said feed further comprises a diluent; wherein said diluent comprises at least one hydrocarbon fluid selected from C6-C13 paraffinic fluids; wherein said oligomerization catalyst is selected from $AlCl_3$, $AlBr_3$, and mixtures thereof; wherein said oligomerization catalyst is an $AlCl_3$-water complex having 0.5 moles of water per mole of $AlCl_3$; wherein said oligomerization reaction zone comprises a continuous stirred tank reactor (CSTR); wherein said oligomerization reaction zone comprises more than one oligomerization reactor in series; wherein the oligomerization conditions in said reactor include a temperature of from about 26 and 60° C. and a pressure of from about atmospheric to about 50 psia; further comprising a step of distillation to remove unreacted monomeric and dimeric species, followed by hydrogenation of the resulting product, without further separation, to saturate the oligomers, followed by recovery of said PAO; and also a preferred embodiment including a composition made by any one or more of the preceding processes, as would be apparent and practicable to one of ordinary skill in the art in possession of the present disclosure, and/or also additional limitations that are more preferred which are selected from at least one of the following: wherein said at least one PAO comprising C30-C36 trimers, C40-C48 tetramers, and C50-C60 tetramers of 1-decene and 1-dodecene; and wherein said at least one PAO is selected from a PAO having a viscosity of about 40 cSt at 100° C., a PAO having a viscosity of about 100 cSt at 100° C.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for producing a polyalphaolefin (PAO) comprising contacting a feed consisting of 40-60 wt. % 1-decene and 60-40 wt. % 1-dodecene with an oligomerization catalyst in an oligomerization reaction zone under oligomerization conditions for a time sufficient to produce either a PAO having a kinematic viscosity of about 40 cSt at 100° C. (ASTM D-445), a viscosity index of at least about 150 (ASTM D-2270), and a pour point of less than or equal to about −42° C. (ASTM D-97), or a PAO having a kinematic viscosity of about 100 cSt at 100° C. (ASTM D-445), a viscosity index of at least about 170 (ASTM D-2270), and a pour point of less than or equal to about −30° C. (ASTM D-97), wherein the PAO has a number average molecular weight of from about 1200 to about 4000 wherein said oligomerization catalyst is selected from the group consisting of $AlCl_3$, $AlBr_3$, and mixtures thereof.

2. The process according to claim 1, wherein said feed comprises 45-55 wt. % 1-decene monomer units and 55-45 wt. % 1-dodecene monomer units, on a molar basis.

3. The process according to claim 1, wherein said feed further comprises a diluent.

4. The process according to claim 3, wherein said diluent comprises at least one hydrocarbon fluid selected from C6-C13 paraffinic fluids.

5. The process according to claim 1, wherein said oligomerization catalyst is an $AlCl_3$-water complex having 0.5 moles of water per mole of $AlCl_3$.

6. The process according to claim 1, wherein said oligomerization reaction zone comprises a continuous stirred tank reactor (CSTR).

7. The process according to claim 1, wherein said oligomerization reaction zone comprises more than one oligomerization reactor in series.

8. The process according to claim 1, wherein said oligomerization conditions include a temperature of from about 26 and 60° C. and a pressure of from about atmospheric to about 50 psia.

9. The process according to claim 1, further comprising a step of distillation to remove unreacted monomeric and dimeric species, followed by hydrogenation of the resulting product, without further separation, to saturate the oligomers, followed by recovery of said PAO.

* * * * *